US009750423B2

(12) United States Patent
Gregg et al.

(10) Patent No.: US 9,750,423 B2
(45) Date of Patent: Sep. 5, 2017

(54) METHOD AND DISPLAY FOR LONG TERM PHYSIOLOGICAL SIGNAL QUALITY INDICATION

(71) Applicant: KONINKLIJKE PHILIPS N.V., Eindhoven (NL)

(72) Inventors: Richard E. Gregg, Westford, MA (US); Saeed Babaeizadeh, Arlington, MA (US); Kathryn Ann Egan, Derry, MA (US); Jean Sarkis, Andover, MA (US); Haisheng Lu, Andover, MA (US); Marianne Messina, Newburyport, MA (US); Elizabeth J. Zengo, Newbury, NH (US); Volker Manfred Hubert, Gaertringen (DE); Stephen Scott Kresge, West Newbury, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/911,030

(22) PCT Filed: Aug. 7, 2014

(86) PCT No.: PCT/IB2014/063761
§ 371 (c)(1),
(2) Date: Feb. 9, 2016

(87) PCT Pub. No.: WO2015/022604
PCT Pub. Date: Feb. 19, 2015

(65) Prior Publication Data
US 2016/0192850 A1    Jul. 7, 2016

Related U.S. Application Data

(60) Provisional application No. 61/865,287, filed on Aug. 13, 2013.

(51) Int. Cl.
A61B 5/04      (2006.01)
A61B 5/044     (2006.01)
A61B 5/00      (2006.01)

(52) U.S. Cl.
CPC .......... *A61B 5/044* (2013.01); *A61B 5/04012* (2013.01); *A61B 5/7203* (2013.01); *A61B 5/7221* (2013.01)

(58) Field of Classification Search
CPC ... A61B 5/044; A61B 5/04012; A61B 5/7221; A61B 5/7203
See application file for complete search history.

(56) References Cited

U.S. PATENT DOCUMENTS 3,909,792 A * 9/1975 Harris .................. A61B 5/0432
345/440
5,827,196 A   10/1998 Yeo et al.
(Continued)

FOREIGN PATENT DOCUMENTS

EP      1406198       4/2004
WO   2011/105462     9/2011
(Continued)

*Primary Examiner* — Mallika D Fairchild (57) ABSTRACT

A medical display system (16) and method display physiological signals. A physiological signal of a patient (14) is received, the physiological signal spanning a period of time. Signal quality of the physiological signal over the period of time is determined. An ECG signal (52) is displayed using a compressed time scale and the determined signal quality (54)n over time is displayed adjacent to the displayed physiological signal.

20 Claims, 6 Drawing Sheets

(56) References Cited

U.S. PATENT DOCUMENTS

2005/0075551 A1* 4/2005 Horn ................. A61B 1/00009
                                                        600/361
2010/0022903 A1   1/2010 Sitzman et al.
2011/0316704 A1  12/2011 Nielsen et al.

FOREIGN PATENT DOCUMENTS

| WO | 2012/099933 | 7/2012 |
| WO | 2012/114262 | 8/2012 |
| WO | 2013/054242 | 4/2013 |
| WO | 2013/059057 | 4/2013 |

* cited by examiner

58 good

FIG. 2B

60 fair

FIG. 2C

62 poor

METHOD AND DISPLAY FOR LONG TERM PHYSIOLOGICAL SIGNAL QUALITY INDICATION

CROSS REFERENCE TO RELATED APPLICATIONS

This application is the U.S. National Phase application under 35 U.S.C. §371 of International Application No. PCT/IB2014/063761, filed Aug. 7, 2014, published as WO 2015/022604 on Feb. 19, 2015, which claims the benefit of U.S. Provisional Patent Application No. 61/865,287 filed Aug. 13, 2013. These applications are hereby incorporated by reference herein.

The present application relates generally to patient monitoring. It finds particular application in conjunction with long term physiological signal quality indication, and will be described with particular reference thereto. However, it is to be understood that it also finds application in other usage scenarios and is not necessarily limited to the aforementioned application.

When a physiological monitoring signal, such as an electrocardiography (ECG) signal, spanning a long term (i.e., more than 1 hour, typically 24 hours) is available to a clinician, it can be challenging to find representative subsets to review for detailed rhythm and morphology analysis. From a compressed time scale where many minutes or hours of the signal can be seen at once, the difference between a poor quality signal and rhythm or morphology changes cannot be determined. Noise and artifacts mask the signal features required to make accurate diagnoses. Further, it is too time consuming to scan all parts of a signal that appear to have potentially clinically important changes. Hence, clinicians need an aid to find good quality signal so searching can be limited to just good quality signal.

The present application provides a new and improved system and method which overcome these problems and others.

In accordance with one aspect, a medical display system for displaying physiological signals is provided. The medical display system includes at least one processor programmed to receive a physiological signal of a patient, the physiological signal spanning a period of time. The at least one processor is further programmed to determine signal quality of the physiological signal over the period of time, display the physiological signal using a compressed time scale, and display the determined signal quality over time and adjacent to the displayed physiological signal.

In accordance with another aspect, a medical display method for displaying physiological signals is provided. The medical display method includes receiving a physiological signal of a patient, the physiological signal spanning a period of time. Further, the method includes determining signal quality of the physiological signal over the period of time, displaying the physiological signal using a compressed time scale, and displaying the determined signal quality over time and adjacent to the displayed physiological signal.

In accordance with another aspect, a graphical user interface (GUI) for displaying physiological signals is provided. The GUI includes a display device displaying a physiological signal of a patient using a compressed time scale. The physiological signal spans a period of time and displayed with insufficient granularity to distinguish between diagnostic features, noise and artifacts. The display device further displays signal quality of the physiological signal over time, the signal quality displayed adjacent to the displayed physiological signal.

In accordance with another aspect, a medical display system for displaying physiological signals is provided. The medical display system includes a receiver unit configured to receive a physiological signal of a patient, the physiological signal spanning a period of time. Further, the medical display system includes a signal quality unit configured determine signal quality of the physiological signal over the period of time. Even more, the medical display system includes a display unit configured to display the physiological signal using a compressed time scale and display the determined signal quality over time and adjacent to the displayed physiological signal.

One advantage resides in determining signal quality from a compressed time scale.

Another advantage resides in separating artifacts from abnormalities at a compressed time scale.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
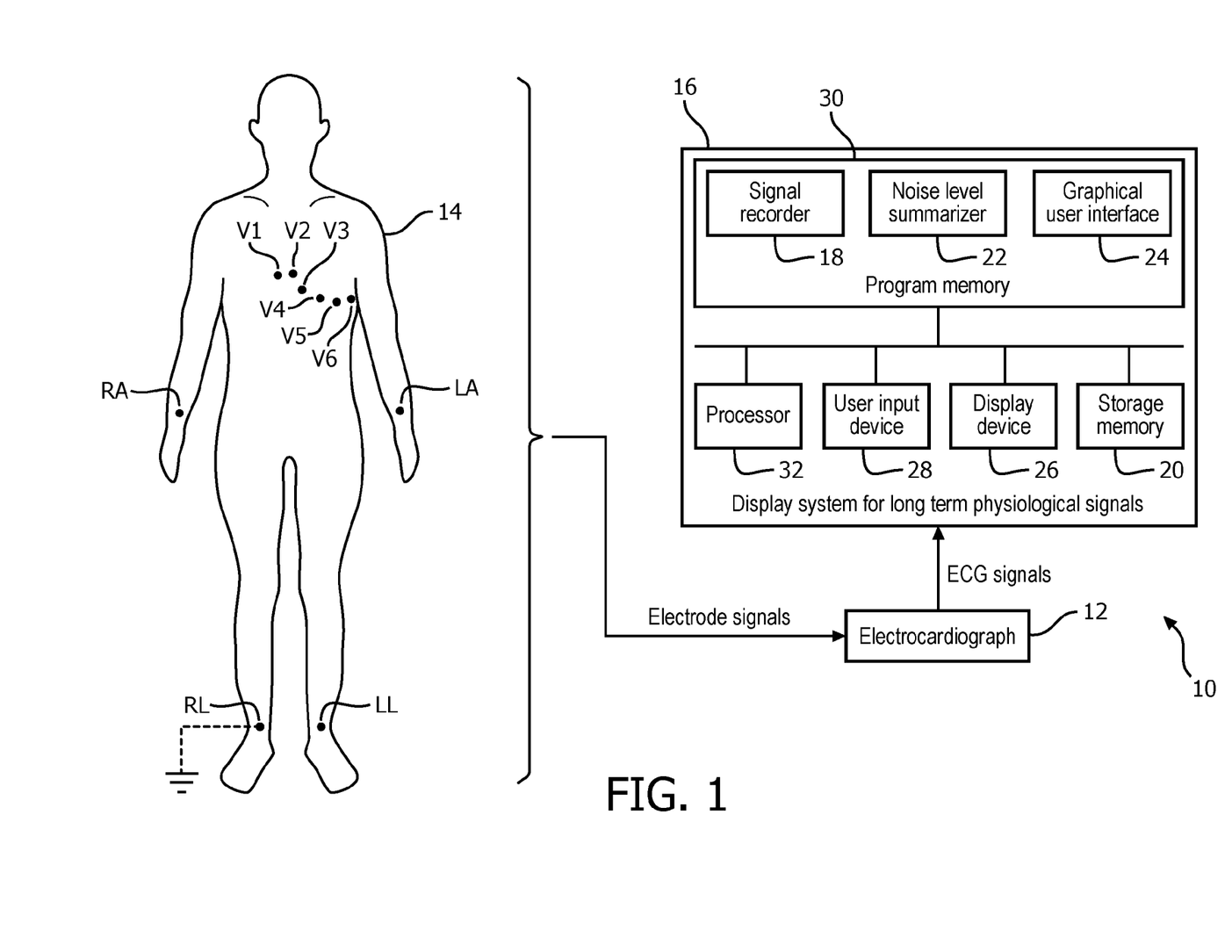
FIG. 1 illustrates a medical system including a display system for displaying long term physiological signals.

With reference to FIG. 1, a medical system 10 includes an electrocardiograph 12 non-invasively measuring the electrical activity of the heart of a patient 14 using electrodes $V_{1-6}$, RA, LA, RL, LL. Each electrode $V_{1-6}$, RA, LA, RL, LL is placed on the patient 14 at a medically appropriate location within some tolerance. From these electrodes $V_{1-6}$, RA, LA, RL, LL, leads (i.e., potential differences) are measured and/or derived. Typically, the electrocardiograph 12 is one of a three-, five-, twelve-, fifteen-, sixteen-, or EASI twelve-lead electrocardiograph.

As illustrated, the electrocardiograph 14 is a twelve-lead electrocardiograph employing ten electrodes $V_{1-6}$, RA, LA, RL, LL for measuring the electrical activity of the heart. A right leg electrode RL serves as a ground for the other electrodes $V_{1-6}$, RA, LA, LL. Lead I is measured from a right arm electrode RA to a left arm electrode LA; lead II is measured from the right arm electrode RA to a left leg electrode LL; and lead III is measured from the left arm electrode LA to the left leg electrode LL. The average voltage V of the right arm electrode RA, the left arm electrode LA and the left leg electrode LL (i.e., Wilson's central terminal) is determined. The other nine leads include six precordial leads derived from potential differences between V and electrodes $V_{1-6}$ and three augmented limb leads aVR, aVL and aVF derived from combinations of leads I, II, and III.

The medical system 10 further includes a display system 16 for displaying long term physiological signals. A long term physiological signal is a physiological signal spanning more than a 1 hour period. Electrocardiography (ECG) signals and impedance-based respiratory signals typically span more than a 1 hour period and are thus typically long term physiological signals.

The display system 16 receives one or more related physiological signals in real-time over a long term (i.e., more than 1 hour), or a historical data set describing the related physiological signals over a long term. Related physiological signals are signals describing the same physiological phenomenon, but from a different perspective, or signals used to diagnosis a common physiological condition, such as arrhythmia. For example, ECG signals corresponding to different leads describe the same physiological phenomenon (i.e., the electrical activity of the heart), but from different angles. As illustrated, the display system 16 receives ECG signals from the electrocardiograph 22. However, other sources of physiological signals are contemplated.

Where the display system 12 receives the physiological signals in real-time, a signal recorder 18 of the display system 12 records the physiological signals in a storage memory 20 of the display system 12 as the physiological signals are received. Otherwise the signal recorder 18 records the historical data set in the storage memory 20.

A noise level summarizer 22 determines the signal quality of the physiological signals over time. The determination of signal quality is a judgment on the ability of a human reader to make an accurate diagnosis with the physiological signals. The more that diagnostic features of the physiological signals are masked by artifacts and the higher artifact levels are, the harder it is for a human reader to make an accurate diagnosis. Further, the higher the noise level, the higher the probability for a diagnostic mistakes and the higher the probability that a human reader will be unable to diagnose abnormal conditions, especially when the abnormal conditions are based on subtle features of the physiological signals.

The signal quality can be determined according to any number of well-known approaches. However, the determined signal quality is typically a combined noise level for all or a subset of the physiological signals. Further, the signal quality can be determined in real-time or on-demand when the signal quality is needed. Even more, the signal quality can be stored in the storage memory 20 as it is determined.

According to one approach to determining the signal quality of the physiological signals, the noise and artifact levels of all of the physiological signals over time are estimated for each of the physiological signals. For example, for ECG signals, the muscle artifact and baseline wander over time are separately estimated for each of the signals. Using the noise and artifact level estimations, the combined noise level of the physiological signals over time is determined by summing the noise and artifact level estimations across all the physiological signals over time. In some instances, hysteresis and/or smoothing are used on the combined noise level over time to prevent fast, short changes in the combined noise level. The combined noise level over time can then be used as the signal quality for the physiological signals.

According to another approach to determining the signal quality of the physiological signals, the noise and artifact levels of a subset of the physiological signals over time are estimated for each physiological signal of the subset. This is suitably performed as described above. Further, the physiological signals of the subset are suitably selected so as to be representative of the other physiological signals excluded from the subset. After estimating the noise and artifact levels, the combined noise level of the subset of physiological signals over time is determined by summing the noise and artifact level estimations across all of the physiological signals of the subset over time. As above, hysteresis and/or smoothing can be used on the combined noise level over time. The combined noise level over time can then be used as the signal quality for the physiological signals.

In some instances, one or more of the physiological signals may temporarily become unavailable (e.g., an electrode is accidently disconnected). In such instances, when estimating the noise and artifact levels according either one of the preceding two approaches, the artifact level of each of these physiological signals is zero over the period of unavailability, and the noise level of each of these physiological signals is a predetermined noise level or the level of the signal over the period of unavailability. Alternatively, the noise level of each of these physiological signals is zero over the period of unavailability, and the artifact level of each of these physiological signals is a predetermined artifact level or the level of the signal over the period of unavailability.

When one of the signals is unavailable, the signal quality should be lower than it would otherwise be. The more signals available, the higher the signal quality should be. As an example, the signal quality should be poor when no signals are available. For the foregoing approaches to determining overall signal quality, this end result is suitably accomplished by setting the predetermined noise or artifact levels so as to penalize overall signal quality when signals are unavailable. Alternatively, for the foregoing approaches to determining overall signal quality, the summations of noise and artifact level estimations can further include the number of unavailable signals (or available signals).

A graphical user interface (GUI) 24 of the display system allows a user of the display system 16 to interact with the display system 16. The GUI 24 uses a display device 26 of the display system 16 to display a plurality of graphical elements to the user. Using a user input device 28 of the display system 16, the GUI 24 allows the user to manipulate these graphical elements. Through manipulation of these graphical elements the user can control aspects of the display system 16.

The GUI 24 allows a user of the display system 16 to display the physiological signals (i.e., a feature of the physiological signals, such as signal intensity) over time using a compressed time scale. Typically, only one of the physiological signals is displayed at any given time. When displaying a physiological signal, the entirety of the signal is typically displayed concurrently. However, it is also contemplated that only a selected subset of the signal is displayed concurrently. To display a portion (i.e., the entirety or a selected subset) of a physiological signal, the portion is typically graphed with the vertical axis corresponding to signal level and the horizontal axis corresponding to time. When the portion of the signal reaches the end of a row, the signal carries over to a new row, typically immediately below the row. A row extends along the horizontal axis from one end of the display area to the opposite end of the display area (left to right for most cultures).

As used herein, a time scale corresponds to the ratio of units of display (e.g., pixels) to units of time (e.g., seconds or minutes). For example, a time scale could be 100 pixels to 1 minute. Further, as used herein, a compressed time scale is a time scale less than needed to analyze a sought after feature (e.g., a diagnostic feature). For example, supposing a time scale of 1000 pixels to 1 minute is the minimum needed to provide sufficient granularity to identify good, fair and poor signal quality, a compressed time scale would be a time scale of less than 1000 pixels to 1 minute. Even more, an enlarged time scale is relative to another time scale (typically a time scale of a displayed signal) and is a time scale larger than the other time scale.

When displaying a physiological signal over time, the signal quality of a portion (i.e., the entirety or a selected subset) of the physiological signal is displayed over time. Where the signal quality for the entirety of a displayed physiological signal is displayed, the signal quality is displayed adjacent to, and temporally aligned with, the physiological signal at the same time scale as the displayed physiological signal. Where the signal quality of a selected subset of a displayed physiological signal is displayed, the signal quality is displayed adjacent to the selected portion at an enlarged time scale as the displayed physiological signal. Typically, the enlarged time scale is such that the signal quality spans the width of the display area.

Any number of approaches for graphically representing the signal quality over time can be employed. In some instances, the signal quality over time is represented as a color bar with like colors representing like signal quality or like classes of signal quality. For example, green, light green, and gray can be used to represent good, fair and poor signal quality, respectively. Alternatives to color, such as height, are also contemplated. In some instances, the signal quality over time is represented as a line graph with like line graph amplitude representing like signal quality or like classes of signal quality. Classes of signal quality can be determined by comparing the signal quality to ranges of signal quality levels corresponding to the different classes. For example, the range of values of the signal quality can be divided into thirds corresponding to good, fair and poor signal quality. Further, in some instances, the signal quality over time is represented as a sequence of symbols and/or patterns of symbols representing signal quality or classes of signal quality. For example, different symbols and/or patterns of symbols can be used to represent good, fair and poor signal quality. Even more, in some instances, the color bar is displayed with a sequence of symbols and/or patterns of symbols representing features affecting signal quality overlaid thereon and temporality aligned therewith. For example, for diagnostic ECG, these relevant features can include supine patient position and electrode position on torso or limbs.

The GUI 24 further allows a user to select an area of a signal quality representation to view a corresponding portion of the physiological signals (all or a subset) at an enlarged time scale. For example, where a selected portion of a physiological system is displayed at 10 pixels to 1 minute, the enlarged time scale could be 1000 pixels to 1 minute. Even more, the corresponding portion of the physiological signal can be displayed over time. For example, where an ECG signal is displayed, a selected portion of the physiological signal can be displayed at a rate of 25 millimeters per second (corresponding to paper speed).

Figure 2A:
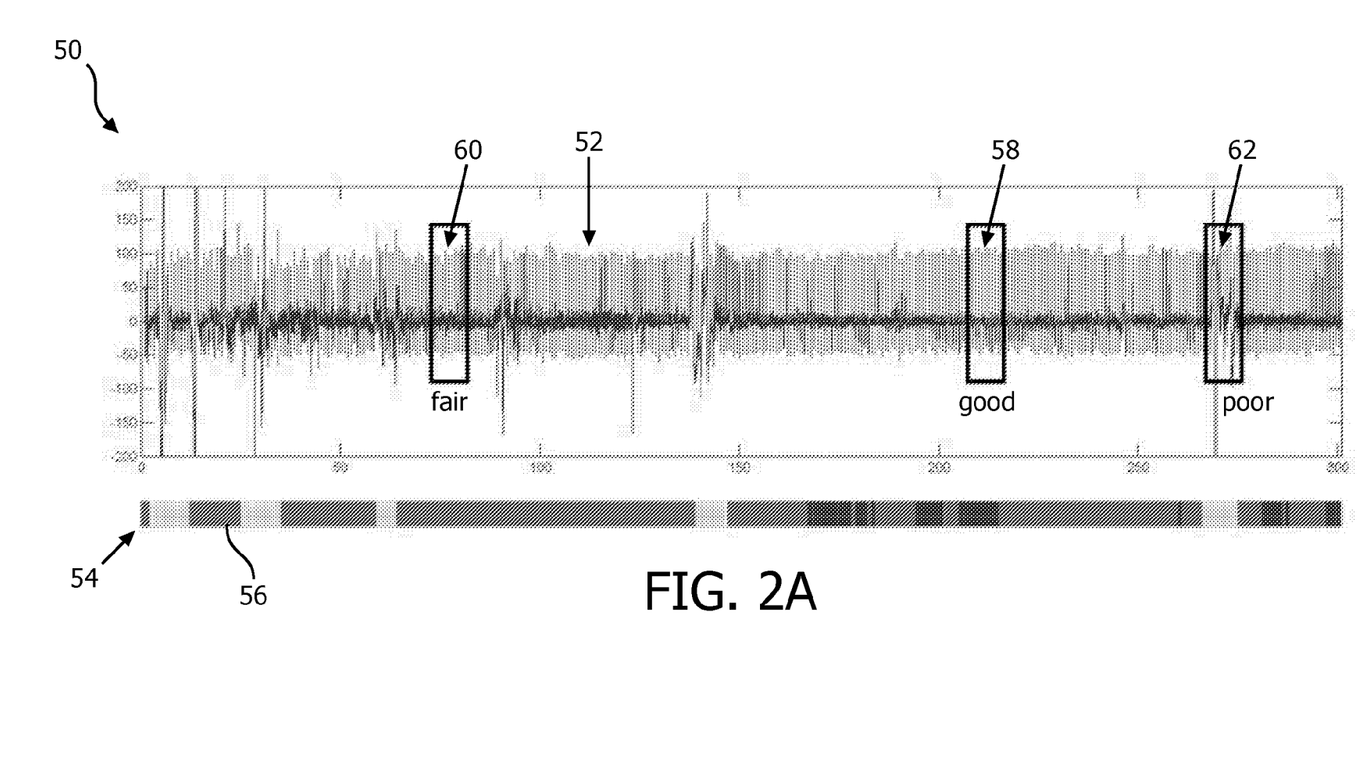
FIG. 2A illustrates an example display of an electrocardiography (ECG) signal, and the corresponding signal quality, over time at a compressed time scale.

With reference to FIGS. 2A-2D, an example display 50 of an ECG signal 52 and the corresponding signal quality 54 over time is illustrated. The ECG signal 52 corresponds to lead II of a twelve-lead electrocardiograph. The vertical axes correspond to signal level (in $10^{-2}$ millivolts) and the horizontal axes correspond to time (in seconds). FIG. 2A illustrates the ECG signal 52, and the corresponding signal quality 54, over time at a compressed time scale. In this time scale, poor signal quality can be inferred, but the difference between good and fair quality cannot be determined. Hence, a color bar 56 representing the signal quality 54 advantageously allows discrimination between poor, good and fair signal quality. The color bar 56 includes, for example, three different colors (e.g., green, light green and gray) corresponding to good, fair and poor signal quality.

Figure 2B:
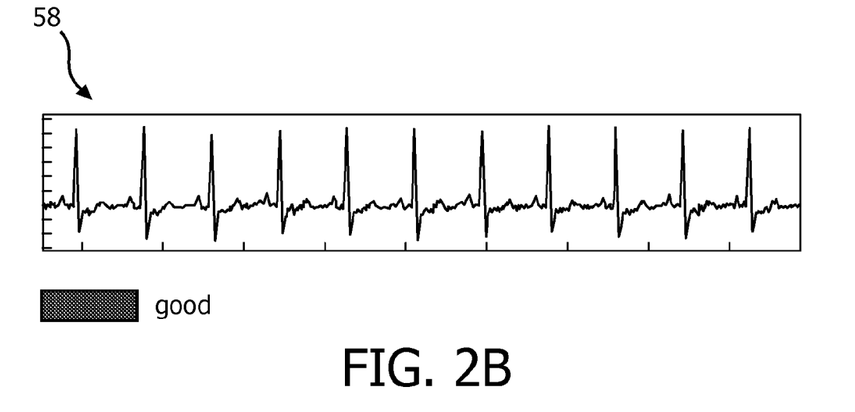
FIG. 2B illustrates a region of the ECG signal of FIG. 2A corresponding to good signal quality at an enlarged time scale.
Figure 2C:
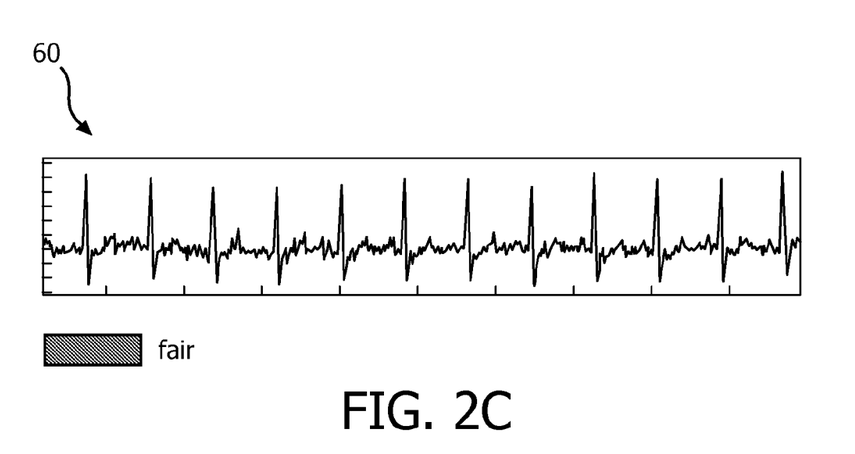
FIG. 2C illustrates a region of the ECG signal of FIG. 2A corresponding to fair signal quality at an enlarged time scale.
Figure 2D:
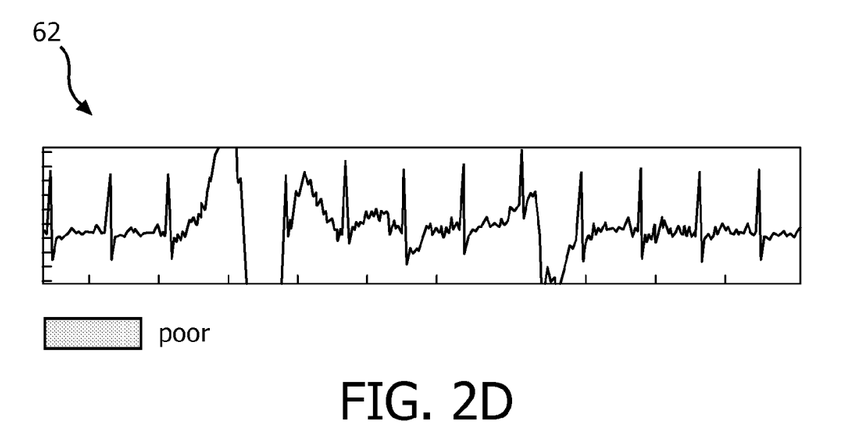
FIG. 2D illustrates a region of the ECG signal of FIG. 2A corresponding to poor signal quality at an enlarged time scale.

For illustrative purposes, regions 58, 60, 62 of the ECG signal 52 corresponding to good, fair and poor signal quality are identified with boxes in FIG. 2A. As can be seen, each region 58, 60, 62 corresponds to a different color on the color bar 56, the color representative of the signal quality of the region. FIGS. 2B-2D illustrate these regions 58, 60, 62 using enlarged time scales. In that regard, FIGS. 2B-2D correspond to good, fair and poor signal quality, respectfully.

Figure 3A:
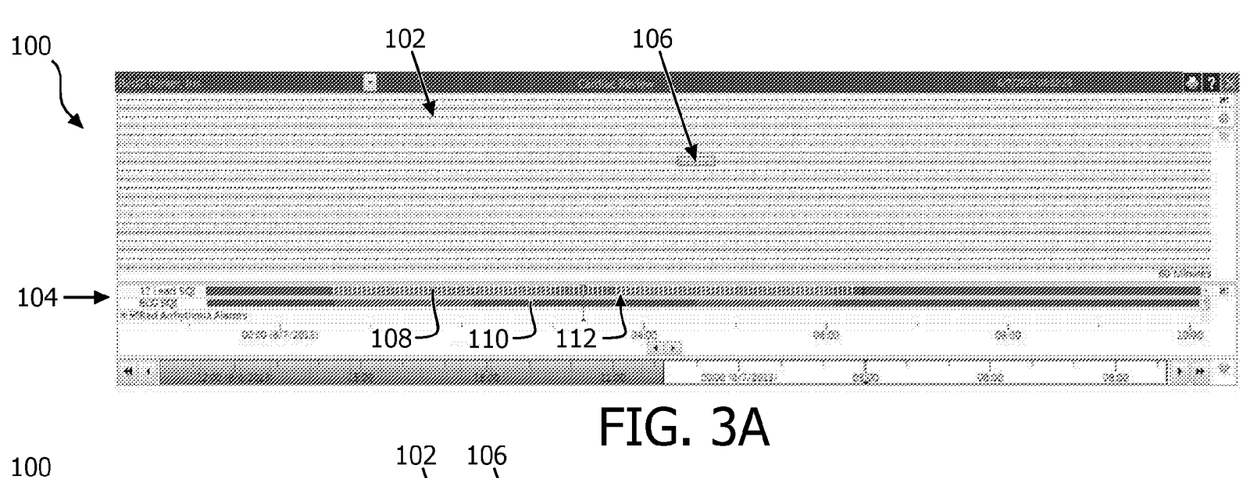
FIG. 3A illustrates another example display of an ECG signal, and the corresponding signal quality, over time at a compressed time scale.

With reference to FIG. 3A, an example display 100 of an ECG signal 102, and the signal quality 104 for a selected region 106 of the ECG signal 102, is illustrated. As illustrated, the region 106 of signal quality displayed is typically selected by moving or drawing a box around the region 106 of the ECG signal 102 for which the display of signal quality 104 is desired. Other approaches to selecting the region 106 are contemplated.

The ECG signal 102 corresponds to lead II of a twelve-lead electrocardiograph. The signal quality 104 depends on not just the displayed ECG signal 102, but also the other unseen ECG signals. Further, the ECG signal 102 is displayed using a compressed time scale commonly used in the medical field and across a plurality of rows, with the vertical axes of the rows corresponding to signal level and the horizontal axes of the lines corresponding to time. As can be seen, the noise level is difficult to see in the ECG signal 102.

The signal quality 104 is displayed using an enlarged time scale that displays the signal quality 104 for the selected region 106 using the full width of the display area. Further, the signal quality 104 is represented by two colors bars 108, 110. Each of the colors bars 108, 110 includes, for example, three different colors (e.g., green, light green and gray) corresponding to good, fair and poor signal quality. Further, each of the colors bars 108, 110 describes a different approach to determining signal quality. The first color bar 108, labeled "12 Lead SQI", represents signal quality determined using all of the ECG signals (i.e., all twelve ECG signals) of a twelve-lead electrocardiogram according to the approach above. The second color bar 110, labeled "ECG SQI", represents signal quality determined using a subset of the ECG signals (i.e., less than the twelve ECG signals) of a twelve-lead electrocardiogram according to the approach above.

A sequence of symbols and/or patterns of symbols 112 (i.e., a hash) is displayed overlaid on the first color bar 108. The hash pattern indicates the twelve ECG signals were diagnostic ECG signals (i.e., generated from 10 electrodes), whereas the lack of the hash pattern indicates that the twelve ECG signals were EASI ECG signals (i.e., generated from 5 electrodes).

Figure 3B:
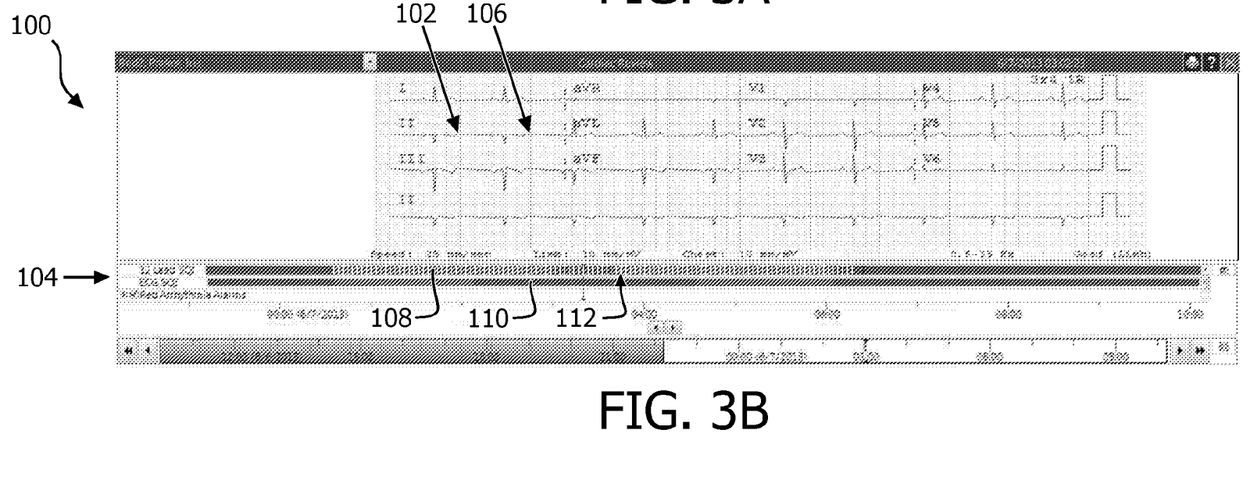
FIG. 3B illustrates the display of FIG. 3A after selection of an area of good signal quality.
Figure 3C:
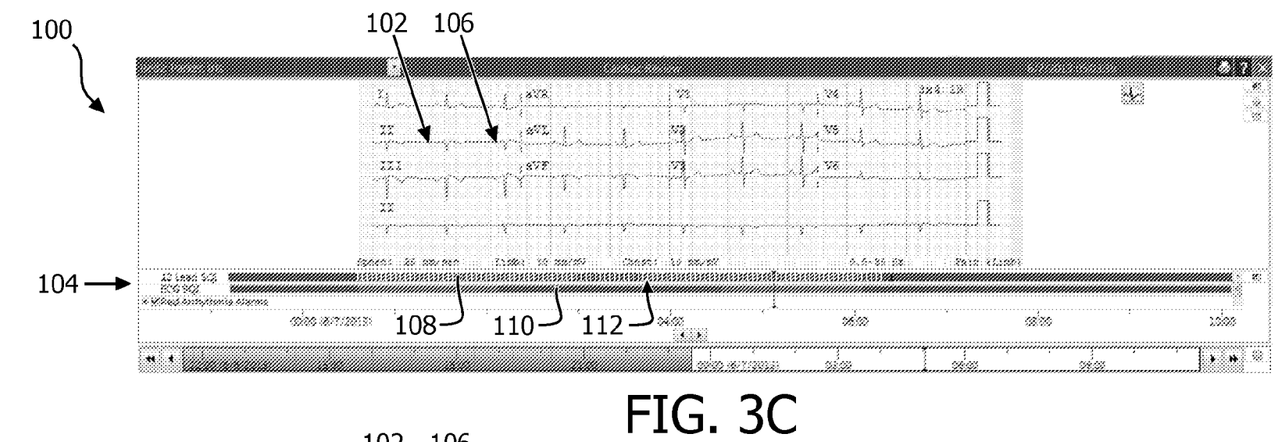
FIG. 3C illustrates the display of FIG. 3A after selection of an area of fair signal quality.
Figure 3D:
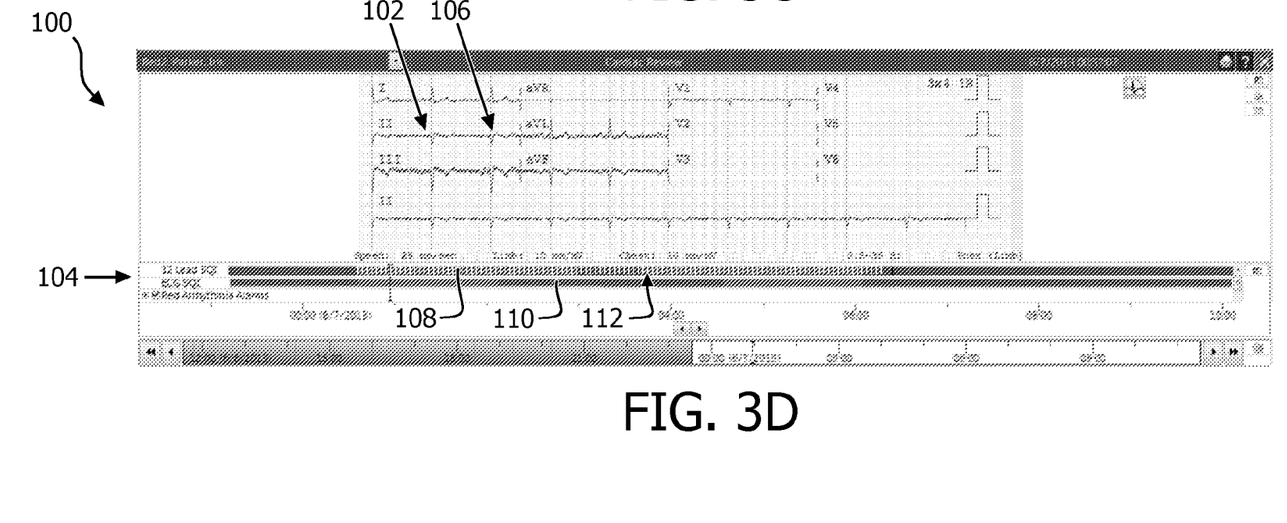
FIG. 3D illustrates the display of FIG. 3A after selection of an area of poor signal quality.

With reference to FIGS. 3B-3C, upon selecting an area of the color bars 108, 110, the displayed ECG signal 102 is replaced with a display of all of the physiological signals for the selected area. As illustrated, a standard 12-lead ECG view is shown. In that regard, the twelve ECG signals are displayed over time for a predetermined period of time, such as 10 seconds. FIG. 3B illustrates the display 100 after selection of an area of good signal quality. The signal quality is good in this case because the noise level is low overall and all leads are available. FIG. 3C illustrates the display 100 after selection of an area of fair signal quality. The signal quality is fair in this case because of high levels of muscle artifact across many leads. FIG. 3D illustrates the display 100 after the selection of an area of poor signal quality. The signal quality is poor in this case because many leads required for a diagnostic interpretation are missing. Namely, chest leads $V_2$ to $V_6$ are missing.

In view of the foregoing, it should be appreciated that the display system 12 finds particular application in conjunction with physiological signals which are often disturbed by noise or artifacts that limit the usefulness of the signals. By displaying signal quality adjacent the physiological signals, the display system 12 helps pick the useful subsets, thereby reducing the time to find useful subsets.

Referring back to FIG. 1, each of the signal recorder 18, the noise level summarizer 22 and the graphical user interface 24 are suitably implemented as processor executable instructions stored on a program memory 30 of the display system 16 and executed by at least one processor 32 of the display system 16. However, it is also contemplated that at least some of the functionality of the signal recorder 18, the noise level summarizer 22 and the graphical user interface 24 is implemented in hardware without the use of a programmable processor. For example, the noise level summarizer 22 can be implemented in an application-specific integrated circuit (ASIC) or a field-programmable gate array (FPGA).

Further, the display system 16 can also be integrated wholly or partially with other devices and/or systems (e.g., ECG monitoring and Holter monitoring systems) that display long term physiological signals over time, especially those where a user needs to pick small subsets of a physiological signal and view the signal at a much larger time scale for diagnostic purposes. For example, the display system 16 can be wholly integrated with the electrocardiograph 12. As another example, the signal recorder 18 can be integrated with the electrocardiograph 12, such that the display system 16 receives stored data from the electrocardiograph 12.

Figure 4:
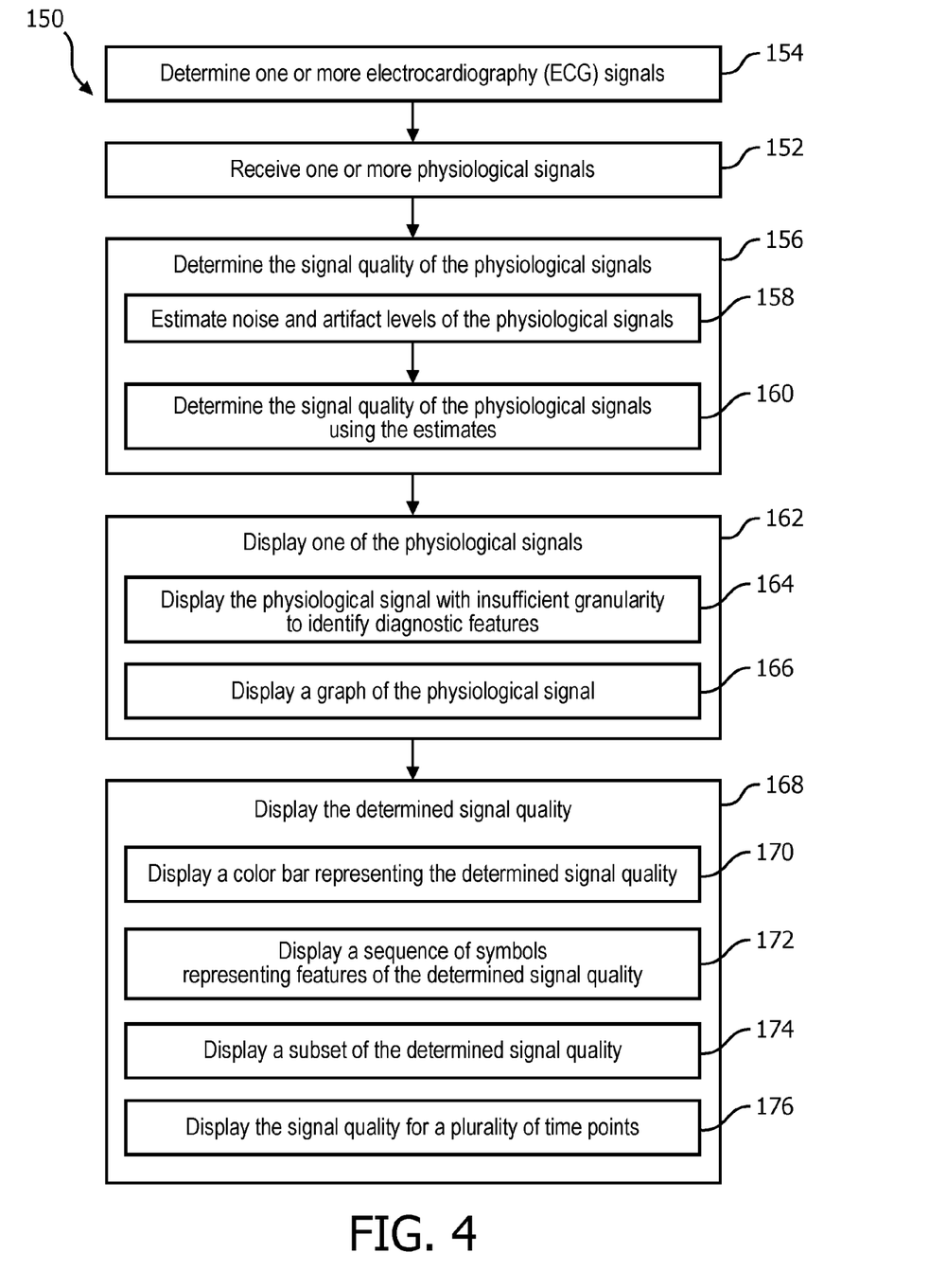
FIG. 4 illustrates a medical display method for displaying long term physiological signals.

With reference to FIG. 4, a medical display method 150 for displaying physiological signals is provided. The method 150 is suitably carried out by the display system 16 of FIG. 1. For example, the method 150 can be embodied by processor executable instructions stored on the program memory 30 of the display system 16 and executed by the at least one processor 32 of the display system.

According to the method 150, one or more physiological signals of a patient are received 152. Each of the physiological signals spans a period of time, typically 24 hours but at least exceeding 1 hour. Where a plurality of physiological signals is received, each of the physiological signals suitably describes a feature for diagnosing a common physiological condition (common to the other physiological signals). In some instance one or more ECG signals are further determined 154 using a plurality of electrodes placed on the patient. In these instances, the received physiological signals can correspond to the ECG signals.

The signal quality of the physiological signals is determined 156 over the period of time. In some instances, the determining 156 includes estimating 158 noise and artifact levels of the physiological signals over the period of time and determining 160 the signal quality of the physiological signals over the period of time by summing the estimated noise and artifact levels over the period of time.

One of the physiological signals is displayed 162 using a compressed time scale. In some instances, the displaying 162 includes displaying 164 the physiological signal with insufficient granularity to identify diagnostic features of the physiological signal. Further, in some the displaying 162 include displaying 166 a graph of the physiological signal, the independent axis corresponding to time and the dependent axis corresponding to signal intensity.

Further, the determined signal quality is displayed 168 over time and adjacent to the displayed physiological signal. In some instances, the displaying 168 includes displaying 170 a color bar representing the determined signal quality, where like colors represent like signal quality or like classes of signal quality, and the length of the bar corresponds to time. Further, in some instances, the displaying 168 includes displaying 172 a sequence of symbols overlaid on the color bar, the sequence of symbols representing features of the physiological signal. Even more, in some instances, the displaying 168 includes displaying 174 the determined signal quality over time for a selected subset of the displayed physiological signal is displayed. Moreover, in some instances, the displaying 168 includes concurrently displaying 176 the determined signal quality for a plurality of time points spanning between the period of time.

As noted above, the method 150 is suitably implemented as processor executable instructions. However, it is also contemplated that the constituent actions (or illustrated blocks) described above can be implemented wholly and/or partially without the use of programmable processors. Further, the constituent actions (or illustrated blocks) can be independent "units", each unit corresponding to a hardware and/or software performing the corresponding functions.

As used herein, a memory includes one or more of: a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; and the like. Further, as used herein, a processor includes one or more of a microprocessor, a microcontroller, a graphic processing unit (GPU), and the like; a user input device includes one or more of a mouse, a keyboard, a touch screen display, a button, a switch, a voice recognition engine, and the like; and a display device includes one or more of a liquid crystal display (LCD) display, a light emitting diode (LED) display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical display system for displaying electrocardiography (ECG) signals, said medical display system comprising:

at least one processor programmed to:
receive an ECG signal of a patient from electrodes placed on the patient, the ECG signal spanning a period of time;
determine signal quality of the ECG signal over the period of time, wherein the period of time exceeds 1 hour;
display the ECG signal acquired over the period of time with a time scale of less than 1000 pixels per 1 minute such that the ECG signal is displayed with insufficient granularity to identify diagnostic features of the ECG signal; and
display the determined signal quality over time and adjacent to the displayed ECG signal.

2. The medical display system according to claim 1, wherein the at least one processor is further programmed to:
estimate noise and artifact levels of the ECG signal over the period of time; and
determine the signal quality of the ECG signal over the period of time by summing the estimated noise and the artifact levels over the period of time.

3. The medical display system according to claim 1, wherein the at least one processor is further programmed to:
receive another physiological signal of the patient spanning the period of time, the ECG signal and the other physiological signal describing features for diagnosing a common physiological condition;
estimate noise and artifact levels of the ECG signal and the other physiological signal over the period of time; and
determine the signal quality of the ECG signal over the period of time by summing the estimated noise and artifact levels over the period of time.

4. The medical display system according to claim 1, wherein the at least one processor is further programmed to:
display a color bar or line graph representing the determined signal quality, wherein like colors or line graph amplitude represent like signal quality or like classes of signal quality, and a length of the bar corresponds to time.

5. The medical display system according to claim 4, wherein the at least one processor is further programmed to:
display a sequence of symbols overlaid on the color bar, the sequence of symbols representing features of the ECG signal.

6. The medical display system according to claim 1, wherein the at least one processor is further programmed to:
display the determined signal quality over time for a selected subset of the displayed ECG signal.

7. The medical display system according to claim 1, wherein the at least one processor is further programmed to:
display a graph of the ECG signal, an independent axis of the graph corresponding to time and a dependent axis of the graph corresponding to signal intensity; and
concurrently display the determined signal quality for a plurality of time points spanning between the period of time.

8. A medical display method for displaying electrocardiography (ECG) signals, said medical display method comprising:
receiving an ECG signal of a patient from electrodes placed on the patient, the ECG signal spanning a period of time;
determining signal quality of the ECG signal over the period of time, wherein the period of time exceeds 1 hour;
displaying the ECG signal acquired over the period of time using a time scale of less than 1000 pixels per 1 minute such that the ECG signal is displayed with insufficient granularity to identify diagnostic features of the ECG signal; and
displaying the determined signal quality over time and adjacent to the displayed ECG signal.

9. The medical display method according to claim 8, further including:
estimating noise and artifact levels of the ECG signal over the period of time; and
determining the signal quality of the ECG signal over the period of time by summing the estimated noise and artifact levels over the period of time.

10. The medical display method according to claim 8, further including:
displaying a color bar representing the determined signal quality, wherein like colors represent like signal quality or like classes of signal quality, and a length of the bar corresponds to time.

11. The medical display method according to claim 8, further including:
displaying a graph of the ECG signal, an independent axis of the graph corresponding to time and a dependent axis of the graph corresponding to signal intensity; and
concurrently displaying the determined signal quality for a plurality of time points spanning the period of time to alert a user to portions ECG signal in which noise and artifacts mask diagnostically significant signal features.

12. At least one processor configured to perform the method according to claim 8.

13. A non-transitory computer readable medium carrying software which controls one or more processors to perform the method according to claim 8.

14. A medical display system for displaying a physiological signal, the medical display system comprising:
at least one electrode placed on a patient, the at least one electrode being configured to obtain a physiological signal of the patient, the physiological signal spanning a period of time;
at least one processor programmed to determine a signal quality of the physiological signal over the period of time, wherein the period of time exceeds 1 hour; and
a display configured to display:
the physiological signal acquired over the period of time with a time scale of less than 1000 pixels per 1 minute such that the physiological signal is displayed with insufficient granularity to identify diagnostic features of the physiological signal and determine a signal quality of the physiological signal over the period of time and rhythm or morphology changes in the physiological signal; and
an indicator indicative of the determined signal quality over time adjacent to, and temporally aligned with, the physiological signal.

15. The medical display system according to claim 14, wherein the at least one processor is further programmed to:
estimate noise and artifact levels of the physiological signal over the period of time; and
determine the signal quality of the physiological signal over the period of time by summing the estimated noise and artifact levels over the period of time.

16. The medical display system according to claim 14, wherein the at least one processor is further programmed to:
receive a second physiological signal of the patient spanning the period of time, the physiological signal and the second physiological signal describing features for diagnosing a common physiological condition;

estimate noise and artifact levels of the physiological signal and the second physiological signal over the period of time; and determine the signal quality of the physiological signal over the period of time by summing the estimated noise and artifact levels over the period of time.

17. The medical display system according to claim 14, wherein the displayed indicator includes a color bar or line graph representing the determined signal quality, wherein like colors or line graph amplitude represent like signal quality or like classes of signal quality, and a length of the bar corresponds to time.

18. The medical display system according to claim 17, wherein the display is further configured to display a sequence of symbols overlaid on the color bar, the sequence of symbols representing features of the physiological signal.

19. The medical display system according to claim 14, wherein the display is further configured to display the determined signal quality over time for a selected subset of the displayed physiological signal.

20. The medical display system according to claim 14, wherein the display is further configured to:
- display a graph of the physiological signal, an independent axis of the graph corresponding to time and a dependent axis of the graph corresponding to signal intensity; and
- concurrently display the determined signal quality indicator for a plurality of time points spanning between the period of time.

* * * * *